United States Patent [19]

Hopmeier et al.

[11] 4,336,031

[45] Jun. 22, 1982

[54] METHOD FOR THE CALIBRATION OF AN OXYGEN SENSING UNIT AND CALIBRATION AGENT THEREFOR

[75] Inventors: Joachim Hopmeier; Helmut Leist; Georg J. Ullrich, all of Freiburg im Breisgau, Fed. Rep. of Germany

[73] Assignee: Hellige GmbH, Freiburg im Breisgau, Fed. Rep. of Germany

[21] Appl. No.: 207,435

[22] Filed: Nov. 17, 1980

[30] Foreign Application Priority Data

Dec. 20, 1979 [DE] Fed. Rep. of Germany ....... 2951325

[51] Int. Cl.$^3$ .............................................. G01N 7/00
[52] U.S. Cl. ................................................. 23/232 R
[58] Field of Search ................. 422/88, 91; 23/232 E, 23/230 R, 232 R

[56] References Cited

U.S. PATENT DOCUMENTS 2,967,092  1/1961  Buchoff et al. .................... 23/232 R

*Primary Examiner*—Peter Chin

[57] ABSTRACT

Disclosed herein is a method for the calibration of a sensing unit for determining the partial pressure of oxygen in contact with the sensing unit. The method is of the type using a zero-calibration solution in which the partial pressure of oxygen is maintained at zero by virtue of a binding agent present in the solution for chemically combining with the oxygen. The essential steps of the method include adding to the solution a color indicator for indicating that the zero-calibration solution contains unspent binding agent, contacting the sensing unit with the zero-calibration solution containing the unspent binding agent and the color indicator, energizing the sensing unit, and adjusting the sensing unit until it indicates zero concentration.

The invention also compasses within its scope a calibration agent for use in the performance of the method for supplying the zero-calibration solution upon dissolution in water, as well as a container for storing the zero-calibration solution.

6 Claims, No Drawings

METHOD FOR THE CALIBRATION OF AN OXYGEN SENSING UNIT AND CALIBRATION AGENT THEREFOR

FIELD OF THE INVENTION

The present invention relates to a method for the calibration of a sensing unit used for determining the partial pressure of oxygen in contact with the sensing unit and to calibration agents for use in the performance of the method.

DESCRIPTION OF THE PRIOR ART

The method of the invention pertains to such methods of the type wherein the sensing unit is firstly brought into contact with a zero-calibration solution in which the partial pressure of the oxygen to be investigated is maintained at zero by virtue of the presence in the solution of a substance descriptively referred to as a binding agent which is capable of chemically binding, i.e. combining with, the investigated substance, and wherein subsequently the sensing unit is put into operating condition and adjusted such that it indicates zero concentration.

In view of the importance of clinical diagnostic methods involving the transcutaneous determination of the partial pressure of oxygen in blood, the method in accordance with the invention is described in more detail further below as implemented for this specific purpose of oxygen pressure determination. However, this method may be implemented for other purposes of oxygen pressure determination as well, e.g., for detecting and determining the pressure of and the partial pressure of oxygen in liquids such as oil and water, e.g. in fishponds or in gases such as methane and other explosive gas mixtures.

In a known method for the calibration of physiological sensing units for determining partial oxygen pressure, the unit is subjected to two known oxygen partial pressures such as, for example first to air whose oxygen partial pressure can be derived from the barometric pressure and then to pure nitrogen whose oxygen partial pressure is zero. However, the use of pure nitrogen is frequently very awkward because of the need for having gas bottles ready which are difficult to handle. For this reason, aqueous solutions of substances which are capable of binding oxygen—so-called zero-calibration solutions—are used instead of nitrogen or of another gas which is free from oxygen. These solutions permit achieving zero oxygen partial pressure at the measuring surface of the sensing unit. For this purpose, the sensing unit is either submersed in the solution, or the measuring surface of the sensing unit is covered with the solution, so that oxygen has no access to it. A calibration method of this type, particularly for sensing units for the transcutaneous determination of oxygen partial pressure in blood is described in German published patent application No. 26 45 736.

Use of the zero-calibration solution has, however, the disadvantage that the solution becomes progressively ineffective. Due to exposure to oxygen whenever the container or bottle in which the solution is stored is opened during use, but also as a result of occasionally inadvertently leaving the container open for significant lengths of time or, alternatively, by continuous oxygen diffusion, particularly through the walls of plastic containers, the capability of the binding agent to combine with oxygen becomes exhausted, as is the case, for example, with sodium sulfite $Na_2SO_3$ or sodium dithionite $Na_2S_2O_4$ when used as the binding agent. Once the total sodium sulfite has been converted into sodium sulfate by combining with oxygen, this binding agent becomes inefficient and the spent zero-calibration solution has become useless.

In order to make certain that a useful zero-calibration solution is used during the calibration step, it has frequently been recommended to freshly prepare the solution. This gives an answer whether the sensing unit operates properly, the method is, however, impractical, costly and timeconsuming.

Particularly in connection with oxygen sensing units used in the medical field, such as, for example, those which continuously measure partial pressure of the oxygen contents in blood, it is necessary for the safety of the patient to be able to check with certainty that the oxygen measuring unit operates reliably. This, in turn, requires checking the calibration conditions, particularly the correct position of the zero point. It is highly desirable that the checking procedure be possible without complicated preparations and without constantly keeping ready otherwise superfluous objects, such as nitrogen-containing gas bottles.

SUMMARY OF THE INVENTION

The problem of ensuring that these conditions prevail has been solved by the method in accordance with the invention and the specific agent used in the performance of the method in a surprisingly simple manner.

The invention makes use of the fact that, as the zero-calibration solution is progressively spent, i.e. for example with successively progressing conversion of sodium sulfite into sodium sulfate, this conversion is accompanied by a shifting of the pH-value of the solution. It was found that it is possible to establish that pH-value at which the capability of binding, i.e. combining with, oxygen has decreased to such an extent that the solution is no longer useful. In the selected example of a solution of sodium sulfite, the pH-value shifts from $pH=9.1$, at which satisfactory binding capability prevails, to $pH=8.4$ constituting the limit at which the capability to bind oxygen is still just acceptable.

Based upon the recognition of a change in pH-value, the invention comprises the addition of a suitable color indicator which responds to the pH-value of the zero-calibration solution, or, alternatively, the use of a mixture of the binding agent with the color indicator when preparing the zero-calibration agent from which, in turn, the zero-calibration solution is to be prepared by dissolving the two contituents in water. The usefulness, i.e. the transition from the unspent condition to the spent condition is then indicated by a change in color. For the above-mentioned example, thymol blue proved to be a suitable indicator, whose color changes from blue toward yellow before the solution has become spent. Thymol blue is the common name for the compound thymolsulfonephtalein $C_{27}H_{30}O_5S$.

It can be seen that, whenever the physiological sensing unit is employed to determine oxygen concentration, the binding agent which combines with oxygen to keep the concentration of free oxygen at zero may be any suitable reducing agent, with sodium sulfite and sodium dithionite being given as typical examples.

In accordance with one broad aspect of the invention, there is provided a method for the calibration of a sensing unit used for determining the partial pressure of oxygen in contact with the sensing unit, using a zero-calibration solution in which the partial pressure of the oxygen is maintained at zero by virtue of a binding agent present in the solution for chemically combining with the oxygen, the method comprising adding to the solution a color indicator for indicating that the zero-calibration solution contains unspent binding agent, contacting the sensing unit with the zero-calibration solution containing the unspent binding agent and the color indicator, energizing the sensing unit, and adjusting the sensing unit until it indicates zero calibration.

The sensing unit to be calibrated may be a sensor for the transcutaneous determination of concentration, as represented by partial pressure of gases within blood or of the oxygen contents in exhaled air. Then, the binding agent may be a reducing agent, such as sodium dithionite $Na_2S_2O_4$ or sodium sulfite $Na_2SO_3$, and the zero-calibration solution is preferably an aqueous solution containing an acid-base indicator, such as thymol blue.

In accordance with a specific example, the zero-calibration solution may comprise, for each 300 ml of water, about 5 to 15 grams, preferably 10 grams of the reducing agent, and about 0.5 to 10 mg, preferably 1 mg of thymol blue.

In accordance with another aspect of the invention, it provides a calibration agent useful with a sensing unit for determining the partial pressure of oxygen in contact with the sensing unit, the agent being employed for preparing zero-calibration solutions and comprising a binding agent capable of chemically binding with the oxygen, in admixture with a color indicator. A calibration solution is then obtained by dissolving the calibration agent in water. In such solution for determining the concentration of oxygen, the binding agent may be a reducing agent, such as sodium dithionite $Na_2S_2O_4$ or sodium sulfite $Na_2SO_3$, as mentioned above, with the color indicator suitably being an acid-base indicator, such as thymol blue.

In accordance with a different aspect, the invention also provides for a container for holding a calibration solution for use with a physiological sensing unit for determining the partial pressure of oxygen in vicinity of the sensing unit, the calibration solution being a solution preferably an aqueous solution of a binding agent capable of chemically combining with the oxygen, in admixture with a color indicator, the container being provided with an area whose color is that of spent solution.

To the extent that the purpose of the sensing units is to determine the partial pressure of oxygen in blood, the sensing units may be adapted either for transcutaneous, for intravenous or for subcutaneous application. No substantial differences for the calibration method are associated with different fields of use.

DETAILED DESCRIPTION

The calibration agent which, when dissolved in water, supplies the calibration solution for conducting the method in accordance with this invention may comprise a mixture of the suitable proportions of the binding agent and of the color indicator. These two basic constituents may be present in the form of powders, of granules or of tablets and may be kept ready for producing the zero-calibration solution prior to each measuring step or, alternatively, in the form of stock useful for several of a series of measuring steps. When oxygen is the chemical substance whose concentration is to be determined by the sensing unit, producing the calibration agent may involve mixing 5 to 15 grams, preferably about 10 grams of sodium sulfite or sodium dithionite with between 0.5 and 10 mg, preferably 1 mg of thymol blue. When preparing the calibration solution, this quantity of calibration agent is dissolved in 300 ml of water, preferably distilled water.

As mentioned above, it was found suitable to provide the container used for storing the zero-calibration solution with a color marking which permits an operator of the unit to check to what extent the calibration solution is still efficient and therefore not yet spent. The two basic conditions can be designated by labeling with legends reading "useful" and "no longer useful" or "spent", suitably associated with two color labels or tags which indicate the two critical colors of the calibration solution. Or, alternatively, it may be sufficient to use only a single colored area, which color characterizes inefficiency of the solution which means the condition that the solution is spent.

The method in accordance with the invention makes certain that only useful zero-calibration solution is used in the calibration step at any given time. Then, it no longer need to be feared that an operator overlooks the inefficiency of the zero-calibration solution. This is of great importance in clinical applications where diagnostic measurements must be performed at maximum speed.

Though the invention is described herein in connection with sensing units for the oxygen determination in blood, it can be seen that the basic concept of adding a color indicator to a binding agent solution may find many fields of application wherever it is desirable to monitor the condition that a zero-calibration solution is spent and thus should no longer be used.

We claim:

1. A method for the calibration of a sensing unit used for determining the partial pressure of oxygen in contact with the sensing unit, using a zero-calibration solution in which the partial pressure of the oxygen is maintained at zero by virtue of a reducing agent present in the solution for chemically combining with the oxygen, the method comprising:
    adding to the solution an acid-base pH color indicator for indicating that the zero-calibration solution contains unspent reducing agent;
    contacting the sensing unit with the zero-calibration solution containing the unspent reducing agent and the acid base pH color indicator;
    energizing the sensing unit; and
    adjusting the sensing unit until it indicates zero concentration.

2. Method according to claim 1, wherein the sensing unit to be calibrated is a sensor for the transcutaneous determination of the partial pressure of oxygen within blood.

3. Method according to claim 1, wherein the sensing unit to be calibrated is a sensor for determining the concentration of oxygen in exhaled air.

4. Method according to claim 1, wherein the reducing agent is selected from the group consisting of sodium dithionite ($Na_2S_2O_4$) and sodium sulfite ($Na_2SO_3$).

5. Method according to claim 1, wherein the acid-base pH color indicator is thymol blue.

6. Method according to claim 5, wherein the zero-calibration solution comprises, for each 300 ml of water, about 10 grams of the reducing agent, and about 0.5 to 10 mg of thymol blue.

* * * * *